US011351033B2

(12) United States Patent
Chary et al.

(10) Patent No.: US 11,351,033 B2
(45) Date of Patent: Jun. 7, 2022

(54) IMPLANTABLE DEVICE FOR TEMPOROMANDIBULAR JOINT AND METHOD OF PRODUCTION THEREOF

(71) Applicants: Manmadha A. Chary, Warangal (IN); Aditya Mohan Alwala, Hyderabad (IN); Giridhar V. Kumar, Hyderabad (IN); Ravi Y. Kumar, Warangal (IN)

(72) Inventors: Manmadha A. Chary, Warangal (IN); Aditya Mohan Alwala, Hyderabad (IN); Giridhar V. Kumar, Hyderabad (IN); Ravi Y. Kumar, Warangal (IN)

(73) Assignee: Manmadha A. Chary, Warangal (IN)

( * ) Notice: Subject to any disclaimer, the term of this patent is extended or adjusted under 35 U.S.C. 154(b) by 123 days.

(21) Appl. No.: 16/628,663

(22) PCT Filed: Jul. 6, 2018

(86) PCT No.: PCT/IB2018/054993
§ 371 (c)(1),
(2) Date: Jan. 4, 2020

(87) PCT Pub. No.: WO2019/008547
PCT Pub. Date: Jan. 10, 2019

(65) Prior Publication Data
US 2020/0129296 A1    Apr. 30, 2020

(30) Foreign Application Priority Data

Jul. 7, 2017  (IN) .............................. 201741023907

(51) Int. Cl.
A61F 2/30          (2006.01)
(52) U.S. Cl.
CPC ........ A61F 2/3099 (2013.01); A61F 2/30942 (2013.01); A61F 2002/30578 (2013.01);
(Continued)

(58) Field of Classification Search
CPC ... A61F 2/2803; A61F 2/3099; A61B 17/8071
See application file for complete search history.

(56) References Cited

U.S. PATENT DOCUMENTS 5,405,393 A * 4/1995 Falkenstrom ......... A61F 2/3099
623/17.17
5,445,650 A * 8/1995 Nealis ................ A61B 17/8071
623/17.17
(Continued)

*Primary Examiner* — Jason-Dennis N Stewart
(74) *Attorney, Agent, or Firm* — Manmadha A. Chary

(57) ABSTRACT

Exemplary embodiments of the present disclosure are directed towards an implantable device for complete replacement of temporomandibular joint comprising of a condyle component to reconstruct a mandibular end of the temporomandibular joint designed for movement within the implantable device with a plate; and a condyle surface where the plate is configured to mechanically secure the condyle component to a ramus surface of a patient undergoing implant with the aid of screws; and the condyle surface polished to generate a mirror effect to reduce the friction in the implantable device and infection rate; a zygomatic arch component to reconstruct a temporal bone (glenoid fossa) of the temporomandibular joint comprising at least one of: a plate; a plurality of multiple threaded counter sink holes; a plurality of conically tapered holes and a zygomatic arch surface, whereby the multiple threaded counter sink holes are structured within the plate; and a fossa component configured to be positioned between the condyle component and the zygomatic arch component to anchor the movement of the temporomandibular joint and the fossa component comprising of a low density biocompatible material made of a polycarbonate which is utilized in the additive manufacturing for the synthesis of implantable device for temporomandibular joint.

11 Claims, 6 Drawing Sheets

(52) U.S. Cl.
CPC .............. *A61F 2002/30962* (2013.01); *A61F 2002/30991* (2013.01); *A61F 2002/30993* (2013.01)

(56) References Cited

U.S. PATENT DOCUMENTS

| | | | | |
|---|---|---|---|---|
| 5,549,680 | A * | 8/1996 | Gordon | A61F 2/3099 623/17.17 |
| 2016/0081806 | A1 * | 3/2016 | Dubois | A61F 2/3099 623/17.17 |
| 2019/0192302 | A1 * | 6/2019 | Mommaerts | A61F 2/3099 |

* cited by examiner

IMPLANTABLE DEVICE FOR TEMPOROMANDIBULAR JOINT AND METHOD OF PRODUCTION THEREOF

TECHNICAL FIELD

The present invention relates to an implantable medical device. In particular the invention relates to customised artificial temporomandibular joint and methods for its production.

BACKGROUND

Trauma, degenerative joint diseases, excessive clenching or grinding of teeth, congenital defects etc. may impair the temporomandibular joint both anatomically and functionally to an extent which might render it unusable. The dysfunctions of the temporomandibular joint are generally corrected through a temporomandibular joint implant to restore normal joint functionality.

However, implants are invasive in nature and may lead to complications, including implant wear and tear, infection, damage of the bones around the joint, necrosis etc. Some prior arts have disclosed temporomandibular joint implants in which the mandibular part consists of a specifically shaped element adapted to be seated in the cavity with a sliding fit. Since each temporomandibular joint has a unique dimension, it is crucial for the implant to correspond to that dimension to function optimally. Ill-fitted implants can prevent the structured load distribution to the surrounding anatomy. This can cause formation of abnormal stress and strain pockets which can result in pain or permanent damage to the surrounding bone structure.

The material used in the production of implants also plays a crucial role in the normal functioning of the deployed prosthesis. Materials which are incompatible with the surrounding anatomy may cause allergic reaction such as facial swelling, neurological problems and other health complications. Some attempts have been made to use biocompatible materials in prosthesis. However, such material has been used in powdered form composed of spherical particles; and can cause infection and blood contamination if not consolidated properly.

In the light of aforementioned discussion there exists a need for an implantable device which can effectively address the concerns related to the temporomandibular joint disorder.

BRIEF SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

Exemplary embodiments of the present disclosure are directed towards an implantable device for temporomandibular joint and method of production thereof.

An exemplary object of the present disclosure is directed towards components being custom made as per the requirement of the patient.

Another exemplary object of the present disclosure is directed towards components being made of non-corrosive materials.

Yet another exemplary object of the present disclosure is directed towards solid implants weighing the same as the normal bone weight of the patient with reduced volume.

An exemplary aspect of the present subject matter is directed towards a condyle component to reconstruct a mandibular end of the temporomandibular joint designed for movement within the implantable device with a plate; and a condyle surface, the plate is designed to mechanically secure the condyle component to a ramus surface of a patient undergoing implant; and the condyle surface polished to generate a mirror effect to reduce the friction in the implantable device and harboring of microbes.

Another exemplary aspect of the present subject matter is directed towards a zygomatic arch component to reconstruct a maxillary end of the temporomandibular joint with a plate; multiple threaded counter sink holes; and multiple tapered holes and a zygomatic arch surface, and the multiple threaded counter sink holes are structured within the plate.

Yet another exemplary aspect of the present subject matter is directed towards a fossa component positioned between the condyle component and the zygomatic arch component to anchor the movement of the temporomandibular joint, and the fossa component comprises of a low density material from at least one of: a polycarbonate. The fossa component is configured to be bonded with ultrasonic welding into the glenoid fossa component which has tapered holes.

BRIEF DESCRIPTION OF DRAWINGS

Other objects and advantages of the present invention will become apparent to those skilled in the art upon reading the following detailed description of the preferred embodiments, in conjunction with the accompanying drawings, wherein like reference numerals have been used to designate like elements, and wherein.

DETAILED DESCRIPTION

Figure 1:
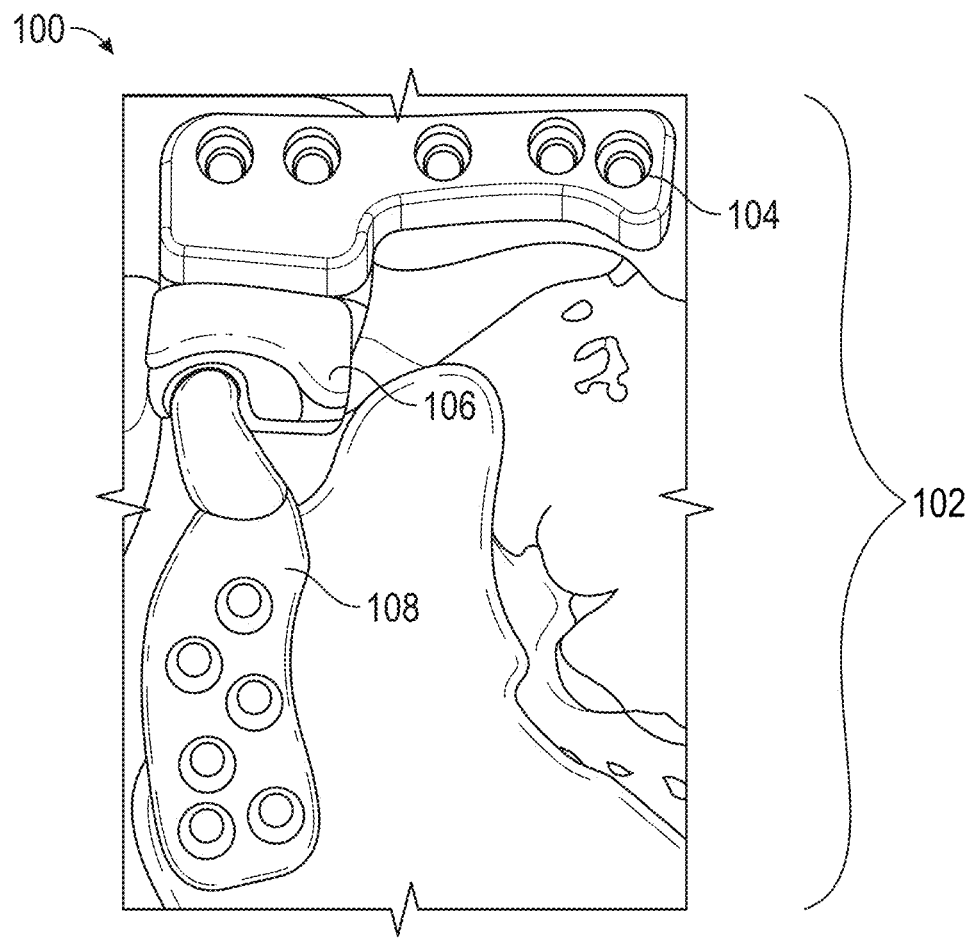
FIG. 1 is an exemplary view of a temporomandibular joint implant fitted to a model.

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item. Further, the use of terms "first", "second", and "third", and the like, herein do not denote any order, quantity, or importance, but rather are used to distinguish one element from another.

In accordance with a non-limiting exemplary embodiment of the present subject matter, FIG. 1 is a representation 100, of an implantable device 102 fitted to a model undergoing TMJ implant (referred to as a patient from now on) which is fabricated by application of a Fused Deposition Modelling (FDM) technique. The implantable device 102 includes a first component (referred from now on as a condyle component 104), employed to reconstruct the mandibular end of a temporomandibular joint (from here on referred to as TMJ). The implantable device 102 further comprises of a second component (referred from now on as a fossa component 106), employed to anchor the movement of the TMJ. The implantable device 102 further comprises of a third component (referred from now on as a zygomatic arch component 108), utilized in the reconstruction of the maxillary end of the TMJ.

Figure 2:
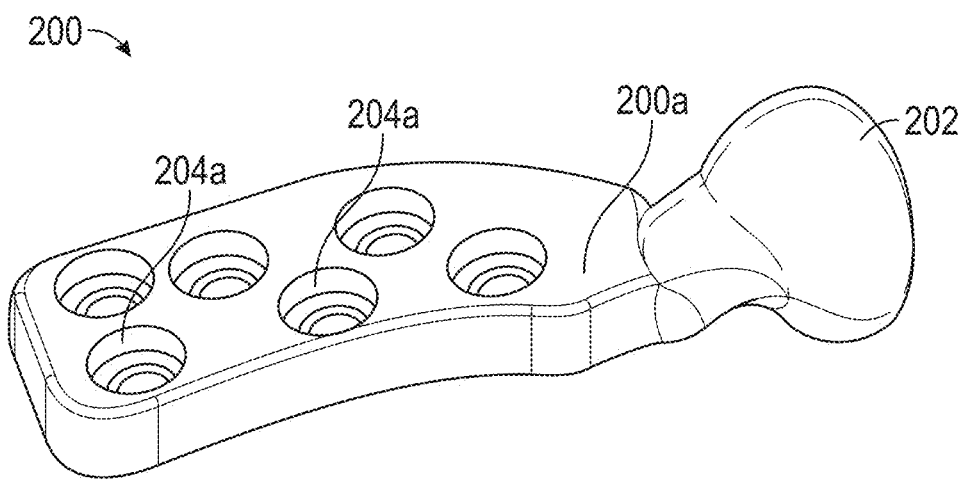
FIG. 2 is a frontal view of the condyle, according to an exemplary embodiment of the present disclosure.

Referring to FIG. 2 is a frontal view 200, of the condyle component, according to an exemplary embodiment of the present disclosure. The condyle component 104, is constructed using biocompatible Titanium alloy (Ti-6AL-4V ELI) and the like, without limiting the scope of the invention. It is designed for movement within the implantable device 102 and includes a plate 200a and a condyle surface 202. The plate 200a is designed to facilitate the mechanical securing of the condyle component 104 to a ramus surface of the model (FIG. 1) with the aid of screws. Furthermore, multiple threaded countersink holes 204a are structured within the plate 200a in a manner to avoid the mandibular branch of the trigeminal nerve upon fastening. The condyle surface 202 of the condyle component 104 is polished to produce a mirror finish to avoid friction during the auxiliary movement of the implantable device 102 and to reduce the rate of infection. Moreover, the condyle component 104 has been constructed as a solid body which is contrary to the natural condyle which is normally hollow in structure. This is to avoid accumulation of foreign particulate matter in order to eliminate chances of infection after the implantable device 102 has been fitted to TMJ of the patient.

Figure 3:
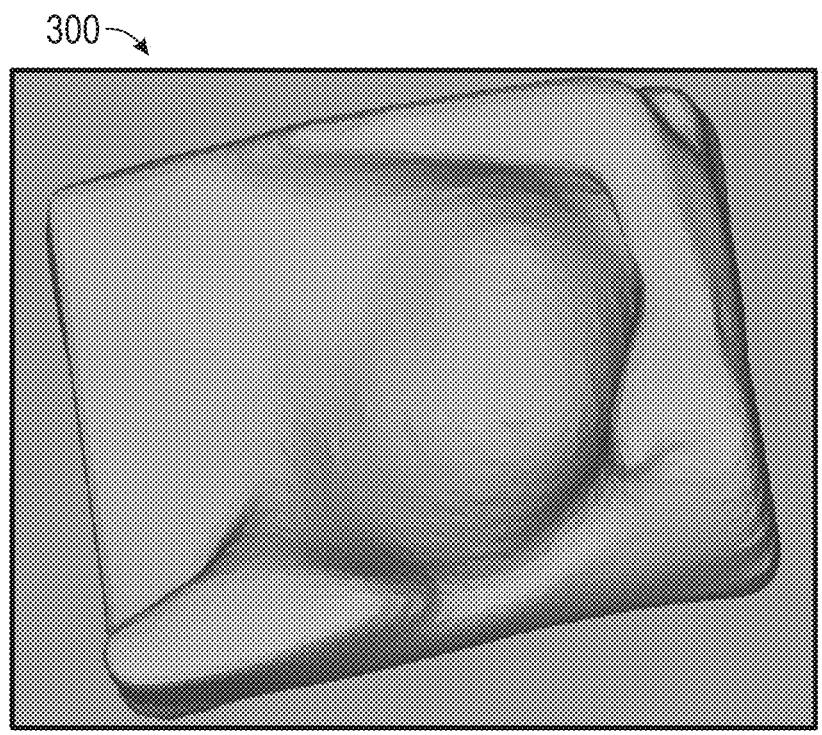
FIG. 3 is a frontal view of the fossa, according to an exemplary embodiment of the present disclosure.

Referring to FIG. 3 is a frontal view 300, of the fossa component, according to an exemplary embodiment of the present disclosure. The fossa component 106 is configured to be made of a low density material not limiting to polycarbonate (PC) with biocompatible certification (ISO 10993 USP Class VI) material by FDM TITAN Ti machine and the like. In one embodiment of the invention, the fossa component 106 is placed between the condyle component 104 and zygomatic arch component 108.

Figure 4:
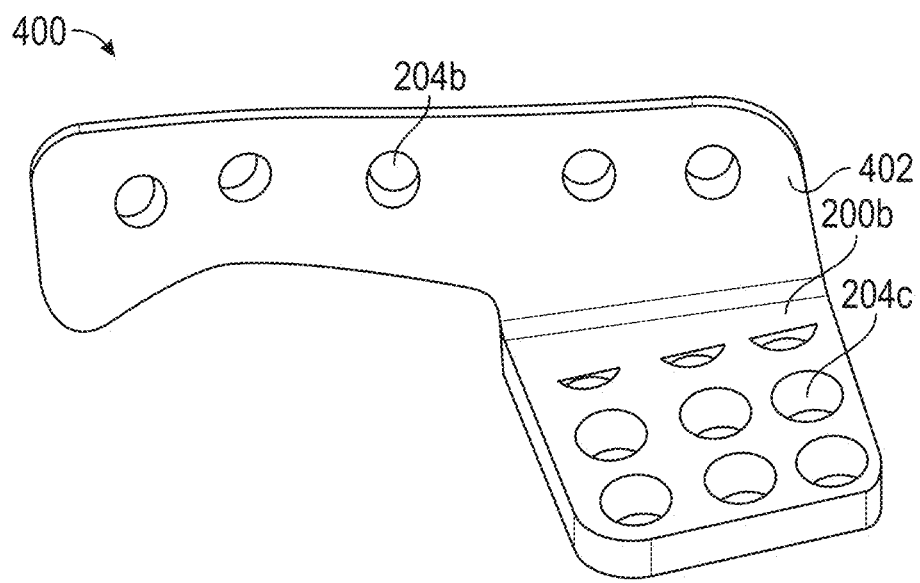
FIG. 4 is a frontal view of the zygomatic arch, according to an exemplary embodiment of the present disclosure.

Referring to FIG. 4 is a frontal view 400, of the zygomatic arch, according to an exemplary embodiment of the present disclosure. The zygomatic arch component 108 is constructed using biocompatible Titanium alloy (Ti-6AL-4V ELI) and the like which is similar to the material utilized for constructing the condyle component 104. In the illustrated embodiment, the zygomatic arch component 108 features a plate 200b, multiple threaded countersink holes 204b, multiple conically tapered holes 204c and a zygomatic arch surface 402. The multiple threaded countersink holes 204b are structured within the zygomatic arch surface 402 and are configured to assist in the fixation of the zygomatic arch component 108 to the zygomatic arch surface of the patient. The multiple conically tapered holes 204c are structured within the plate 200b and are configured to assist in the fixation of the fossa component 106 to the zygomatic arch component 108 by the application of techniques not limiting to, ultrasonic welding, and the like.

One of the key elements of the present invention is a method of the fabrication of the fossa component 106 by replicating the structure of the patient's anatomy. The steps involved in the aforementioned method have been illustrated in FIG. 6B.

Figure 5:
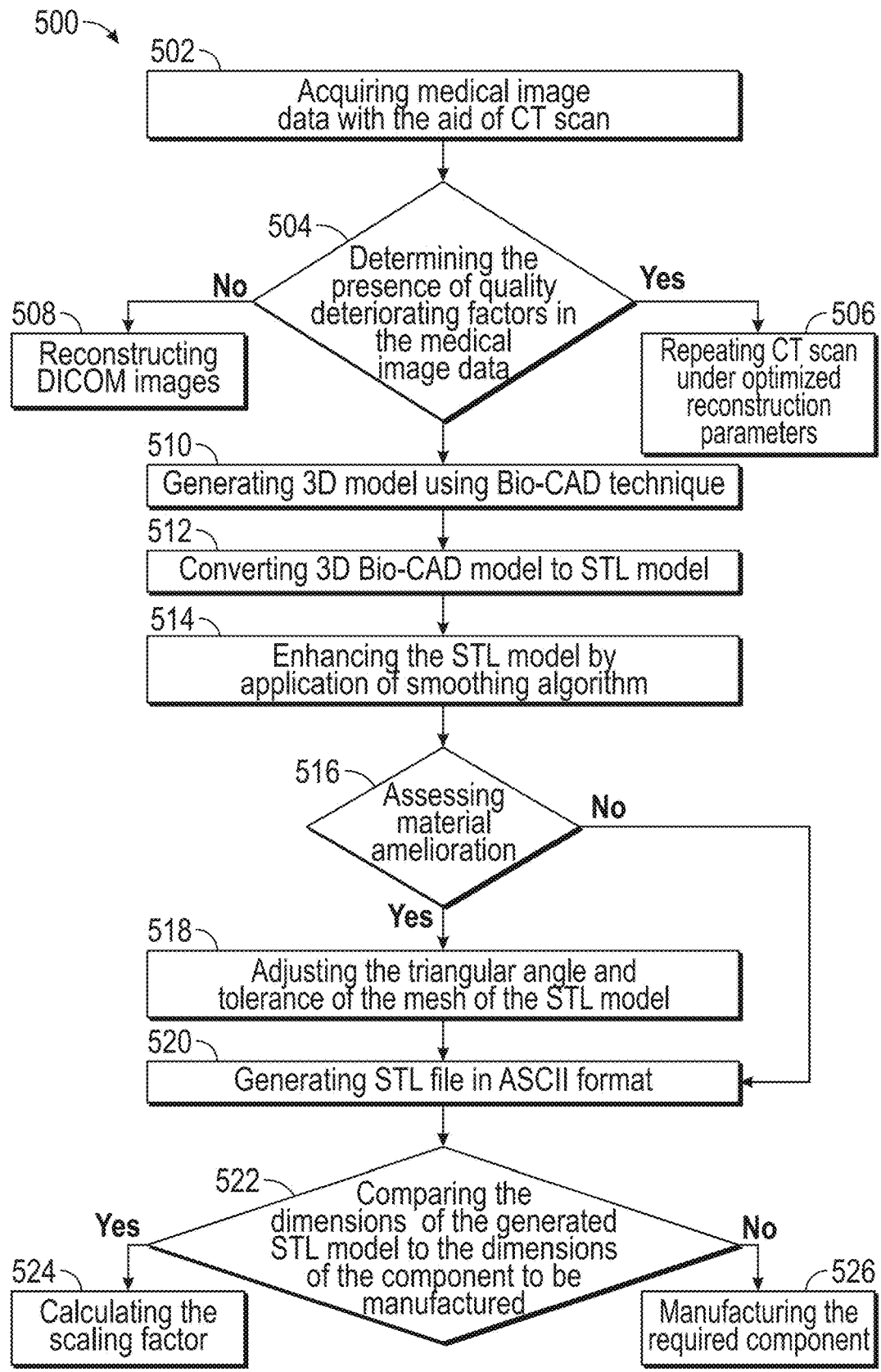
FIG. 5 is a flow chart illustrating a method for production of an implantable device for temporomandibular joint, according to an exemplary embodiment of the present disclosure.

Referring to FIG. 5 is a flow chart 500, illustrating a method for production of an implantable device for temporomandibular joint, according to an exemplary embodiment of the present disclosure, according to an exemplary embodiment of the present disclosure. In step 502, medical image data is acquired with the aid of a Computed Tomography (CT) scan. In step 504, it is determined whether the quality deteriorating factors are present in the medical image data. If the presence of quality deteriorating factors is ascertained, then the CT scan of step 506 is repeated under optimized reconstruction parameters to eliminate them and to augment the dimensional accuracy of the medical image data. Some of the quality deteriorating factors include beam hardening effect, image noise, radiation dose, staircase effect etc. however, other quality deteriorating factors associated with such scanning techniques and well known in the art may also be present. If the determination to step 504 is no, then at step 508 Digital Imaging and Communications in Medicine (DICOM) images are reconstructed using the medical image data. In step 510, a three-dimensional (3D) model is generated using the bio-medical computer aided design (Bio-CAD) technique. The elimination of the quality deterioration factors is crucial since the attributes of the medical image data directly affects the attributes of the 3D model generated in step 510. In step 512, the 3D Bio-CAD model is converted to stereolithography (STL) model for facilitating the fabrication of the required components of the implantable device 102. In step 514, the STL model is further improved by application of the smoothing algorithm. Smoothing of the STL model helps in reducing friction between various components of the implantable device 102 during auxiliary movement of the TMJ. The smoothing algorithm involves the identification of contour data points by slicing of the STL model and generating the common layer interface (CLI) file. These CLI files are then smoothened by application of the Fast Fourier Transform (FFT) algorithms. In step 516, the necessity of material amelioration is assessed. Material adaptation involves trimming and filling operations in order to ameliorate the STL model. If amelioration is required, then in step 518, the triangular angle and tolerance of the mesh of the STL model can be adjusted. Though the methodology employed in steps 514 and 518 has been adapted to accommodate the requirement of the present invention, other arrangements may also be used without limiting the scope of the invention. If in step 516, material amelioration is not required, then in step 520, a STL file in an American standard code for information interchange (ASCII) format is generated. In step 522, the dimensions of the STL model are compared to the measurement of the component to be manufactured. If any error is observed in step 522, then in step 524, a scaling factor is calculated. If not, then at step 526, the required component is manufactured to match the dimensions of the anatomy of the specific patient.

Figure 6A:
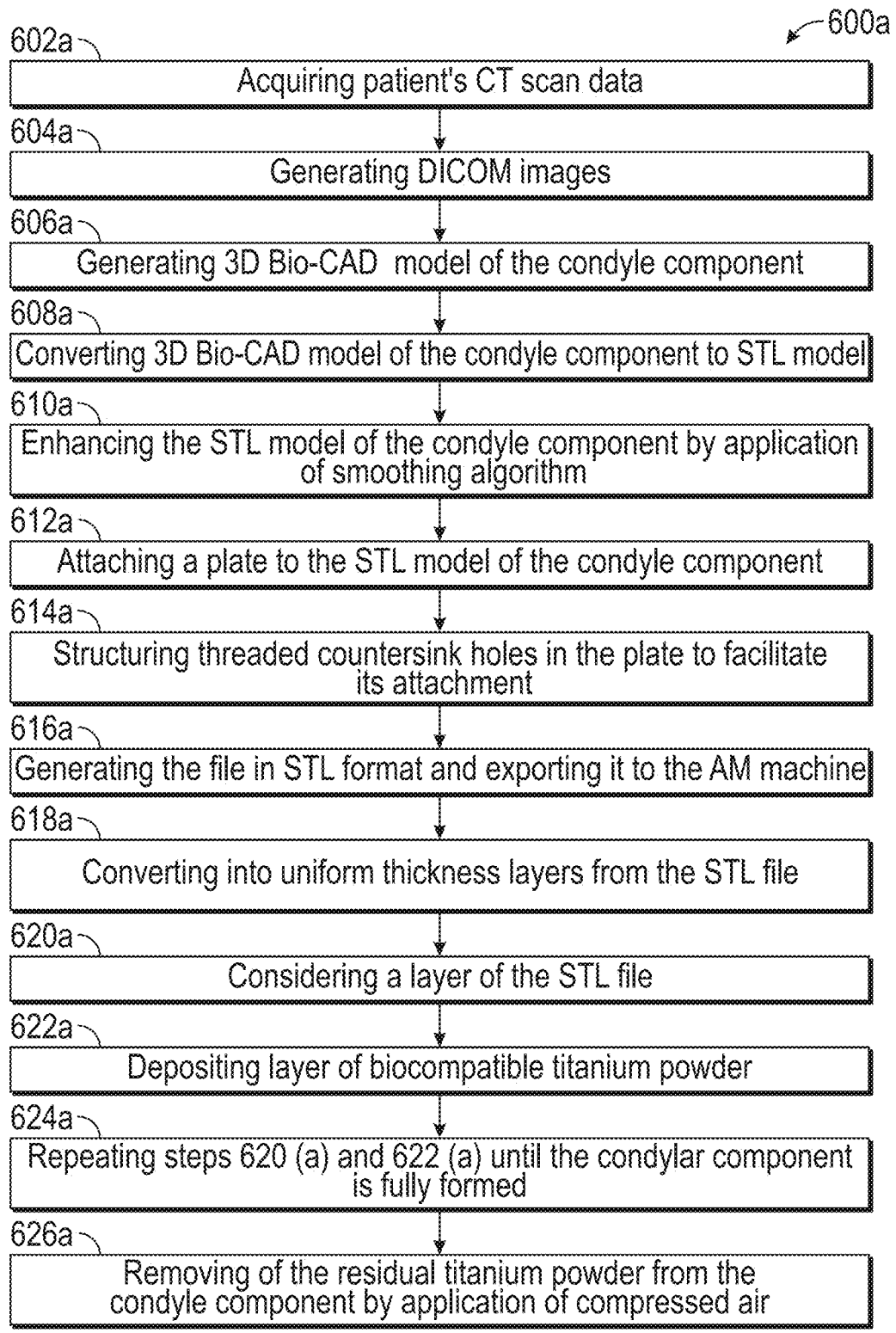
FIG. 6A is a flow chart illustrating the steps involved in the construction of the condyle component, according to an exemplary embodiment of the present disclosure.

FIG. 6A is a flow chart 600a, illustrating the steps followed in the construction of the condyle component, according to an exemplary embodiment of the present disclosure. In step 602a, the patient's CT scan data is acquired for facilitating the generation of DICOM images which takes place in step 604a. In step 606a, 3D Bio-CAD model of the condyle component 104 is generated. In step 608a, the 3D Bio-CAD model is converted to the STL model for facilitating the fabrication of the condyle component 104 of the implantable device 102. In step 610a, the STL model of the condyle component 104 is further improved by application of the smoothing algorithm. In step 612a, the plate 200a (FIG. 2) is coupled to the condyle surface 202 (FIG. 2) to aid the fixing of the fossa component 106 to the condyle component 104. In step 614a, multiple threaded countersink holes 204a (FIG. 2) are structured within the plate 200a (FIG. 2) to facilitate the mechanical securing of the fossa component 106 to the condyle component 104. In step 616a, a file is generated in the STL format and exported to an Additive Manufacturing (AM) machine. In step 618a, the STL file is converted into several layers of uniform thickness. In step 620a, a layer of the STL file is considered for further action. In step 622a, deposition of a first layer of the biocompatible Titanium alloy powder is facilitated on the 3D printed condyle component 104. The steps 620a and 622a are repeated sequentially until the patient specific dimensions of the condyle component 104 are achieved. In step, 626a, the residues of the biocompatible Titanium alloy powder are removed with the aid of compressed air to eliminate the risk of post-operative complications.

Figure 6B:
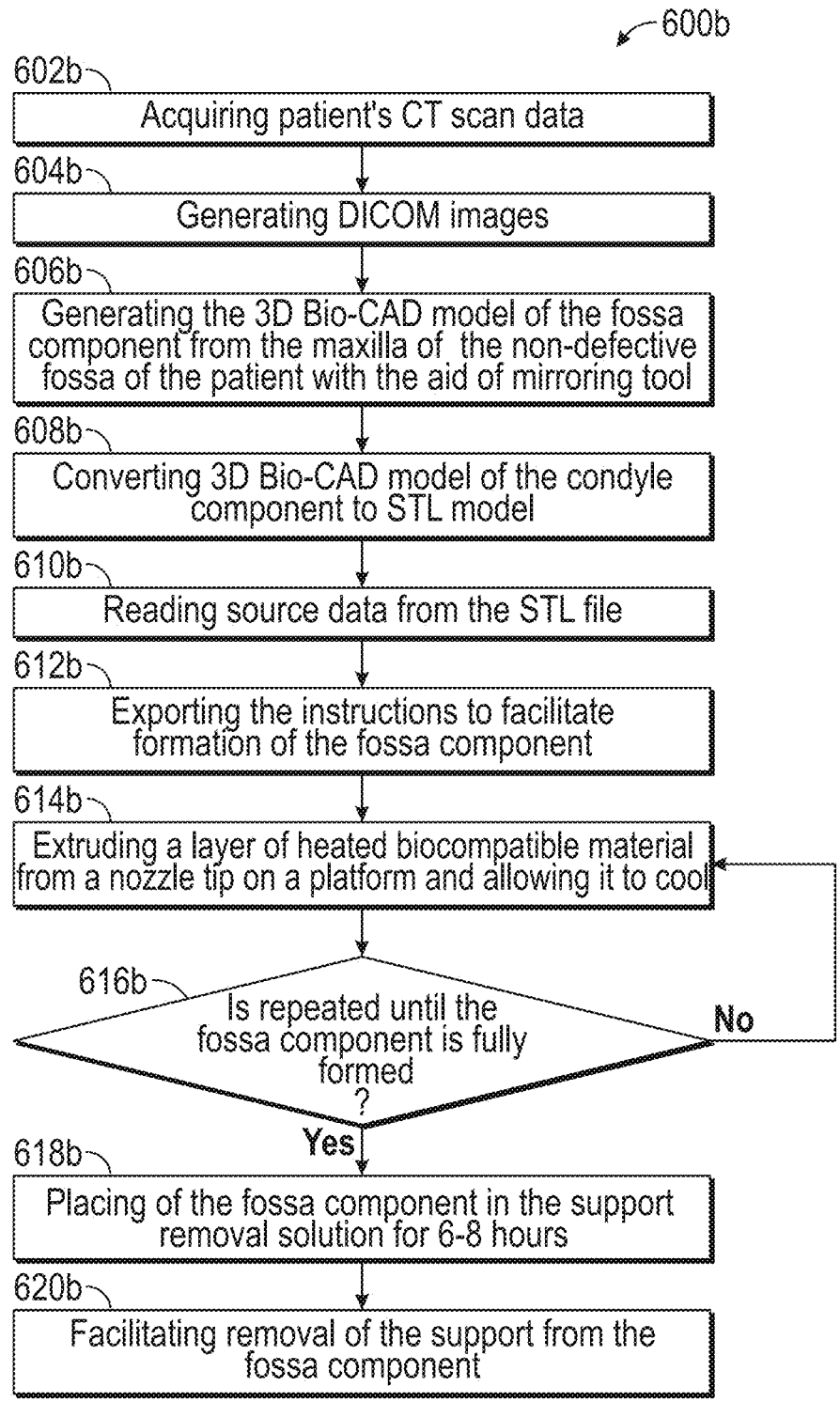
FIG. 6B is a flow chart illustrating the steps involved in the construction of the fossa component, according to an exemplary embodiment of the present disclosure.

FIG. 6B is a flow chart 600b, illustrating the steps involved in the construction of the fossa component, according to an exemplary embodiment of the present disclosure. In step 602b, the patient's CT scan data is acquired for facilitating the generation of DICOM images which takes place in step 604b. In step 606b, 3D Bio-CAD model of the fossa component 106 is generated from the maxilla of the non-defective fossa of the patient with the aid of mirroring tool. In step 608b, the 3D Bio-CAD model is converted to the STL model for facilitating the fabrication of the fossa component 106 of the implantable device 102. In step 610b, the STL model data is read from the STL file, in step 612b, the data is exported to the AM machine for initiating the fabrication of the fossa component 106. In step 614b, the first layer of the PC material is deposited on the platform of the AM machine, followed by subsequent cooling to provide strength to the fossa component 106. The step 614b is repeated until the dimensions of the fossa component of the patient are duplicated. In step 618b, the 3D printed fossa component 106 is placed in support removal solution for a period of 6-8 hours. In step 620b, supports are removed from the fossa component 106. This procedure ensures that that final design of the fossa component 106 is a duplicate of the patient's fossa structure.

Figure 6C:
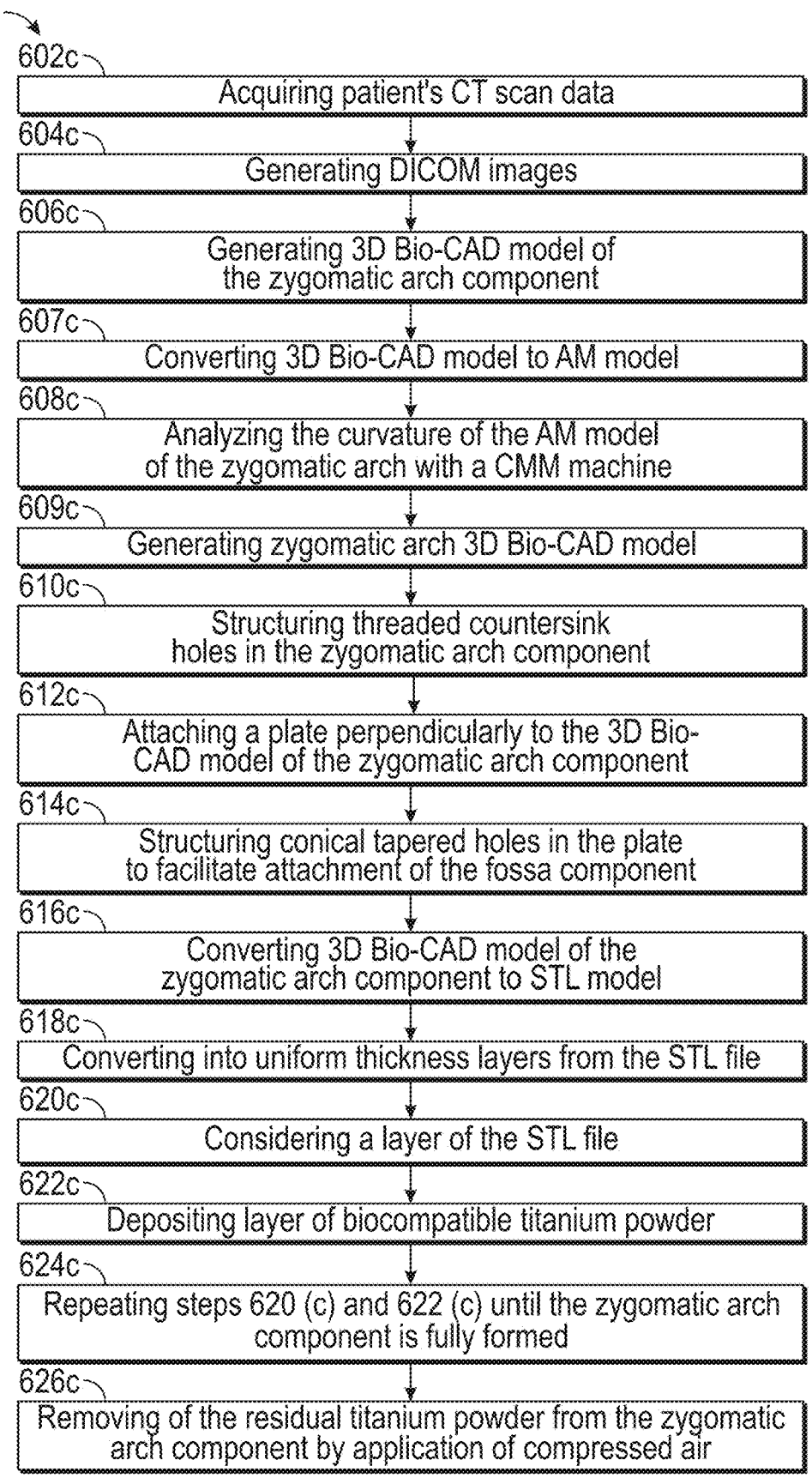
FIG. 6C is a flow chart illustrating the steps involved in the construction of the zygomatic arch component, according to an exemplary embodiment of the present disclosure.

FIG. 6C is a flow chart 600c, illustrating the steps followed in the construction of the zygomatic arch component, according to an exemplary embodiment of the present disclosure. In step 602c, the patient's CT scan data is acquired for facilitating the generation of DICOM images which takes place in step 604c. In step 606c, 3D Bio-CAD model of the zygomatic arch component 108 is generated. In step 607c, the 3D Bio-CAD model of the zygomatic arch component 108 is converted to an AM model. In step 608c, the curvature of the AM model of the zygomatic arch component 108 is analyzed with the aid of a Coordinate Measuring Machine (CMM). This probe is necessary to determine the coordinates of the zygomatic arch component 108 to render a precisely designed model. In step 609c, the 3D Bio-CAD model of the zygomatic arch component 108 is generated. In step 610c, multiple threaded countersink holes 204b are structured within the zygomatic arch surface 402. In step 612c, a plate 200b is attached perpendicularly to the zygomatic arch surface 402 to facilitate the mechanical securing of the fossa component 106 to the zygomatic arch component 108. In step 614c, a set of conically tapered holes 204c are structured within the plate 200b. In step 616c, the 3D Bio-CAD model of the zygomatic arch component 108 is converted to a STL file format. In step 618c, the STL file is converted into several layers of uniform thickness. In step 620c, a layer of the STL file is considered for further action. In step 622c, deposition of a first layer of the biocompatible Titanium alloy powder is facilitated on the 3D printed zygomatic arch component 108. The steps 620c and 622c are repeated sequentially until the desired dimensions of the zygomatic arch component 108 are achieved. In step, 626c, the residues of the biocompatible Titanium alloy powder are removed with the aid of compressed air to eliminate the risk of post-operative complications.

Although the present disclosure has been described in terms of certain preferred embodiments and illustrations thereof, other embodiments and modifications to preferred embodiments may be possible that are within the principles and spirit of the invention. The above descriptions and figures are therefore to be regarded as illustrative and not restrictive.

Thus the scope of the present disclosure is defined by the appended claims and includes both combinations and sub combinations of the various features described herein above as well as variations and modifications thereof, which would occur to persons skilled in the art upon reading the foregoing description.

What is claimed is:

1. An implantable device for temporomandibular joint comprising of:
   a condyle component to reconstruct a mandibular end of the temporomandibular joint designed for movement within the implantable device comprising at least one of: a plate; and a condyle surface, whereby the plate is configured to mechanically secure the condyle component to a ramus surface of, a patient undergoing implant with the aid of screws; and the condyle surface is polished to generate a mirror effect to reduce friction in the implantable device and microbes harboring in the implantable device;
   a zygomatic arch component to reconstruct a maxillary end of the temporomandibular joint comprising at least one of: a plate; a plurality of multiple threaded counter sink holes; a plurality of conically tapered holes and a zygomatic arch surface, whereby the plurality of multiple threaded counter sink holes are structured within the plate; and
   a fossa component configured to be positioned between the condyle component and the zygomatic arch component to anchor the movement of the temporomandibular joint, whereby the fossa component comprises of a low density biocompatible material namely a polycarbonate which is utilized in the additive manufacturing for the synthesis of implantable device for temporomandibular joint.

2. The device of claim 1, wherein the condyle component includes at least one of: biocompatible Titanium alloy (Ti-6AL-4V ELI).

3. The device of claim 1, wherein zygomatic arch component is constructed utilizing a biocompatible Titanium alloy (Ti-6AL-4V ELI).

4. The device of claim 1, wherein a plurality of conically tapered holes are structured within the plate perpendicular to the zygomatic arch surface and are configured to assist in the fixation of the fossa component.

5. The device of claim 1, wherein a multiple threaded countersink holes are configured to assist in the fixation of the zygomatic arch component and the zygomatic arch of the patient undergoing implant.

6. The device of claim 1, wherein the zygomatic arch component is connected to the fossa component through ultrasonic welding.

7. The device of claim 1, wherein the condyle component is constructed as a solid body.

8. The device of claim 1, wherein a multiple threaded countersink holes are structured within the plate of the condyle component in a manner to avoid a mandibular branch of a trigeminal nerve upon fastening.

9. A method for production of an implantable device for temporomandibular joint comprising of:
    acquiring a medical image data with the aid of a Computed Tomography (CT) scan and determining a presence of quality deteriorating factors from at least one of: beam hardening effect; image noise; radiation dose; staircase effect; and partial volume effect in the medical image data, whereby upon ascertaining the presence of the quality deteriorating factors, the CT scan is repeated under optimized reconstruction parameters to eliminate the quality deteriorating factors and to augment a dimensional accuracy of the medical image data else Digital Imaging and Communications in Medicine (DICOM) images are reconstructed using the medical image data;
    generating a three dimensional model of a condyle component, a fossa component, and a zygomatic arch component using a bio-medical computer aided design (Bio-CAD) technique which is converted to a stereolithography (STL) model for facilitating the fabrication of the required components of the implantable device, whereby the STL model is improved by application of the smoothing algorithm involving an identification of contour data points by slicing of the STL model and generating a common layer interface (CU) file which are smoothened by an application of the Fast Fourier Transform (FFT) algorithms; and
    adaptation of materials involving trimming and filling operations in order to ameliorate the STL model by adjusting a triangular angle and tolerance of a mesh of the STL model else an STL file is generated in an American standard code for information interchange (ASCII) format, whereby dimensions of the STL model are compared to the measurements of a required component to be manufactured, calculating a scaling factor by correction of a scaling error before the manufacturing of the required component.

10. The method of claim 9, wherein the manufacturing of at least one of: the condyle component, the fossa component; and the zygomatic arch component manufactured to match the dimensions of the anatomy of the patient.

11. The method of claim 1, wherein a 3D Bio-CAD model of the fossa component is generated from a maxilla of a non-defective fossa of the patient undergoing implant with the aid of mirroring tool.

* * * * *